United States Patent
Seelmann-Eggebert et al.

(10) Patent No.: US 11,540,513 B2
(45) Date of Patent: Jan. 3, 2023

(54) STABILIZATION OF PARTICLES COATED WITH NON-AMPHOTERIC, QUATERNIZABLE AND WATER-SOLUBLE POLYMERS USING A DISPERSING COMPONENT

(71) Applicant: BASF SE, Ludwigshafen am Rhein (DE)

(72) Inventors: Hans-Peter Seelmann-Eggebert, Limburgerhof (DE); Joachim Bentele, Ludwigshafen (DE); Simon Poulton, Ludwigshafen (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/472,531

(22) PCT Filed: Dec. 21, 2017

(86) PCT No.: PCT/EP2017/084061
§ 371 (c)(1),
(2) Date: Jun. 21, 2019

(87) PCT Pub. No.: WO2018/115266
PCT Pub. Date: Jun. 28, 2018

(65) Prior Publication Data
US 2019/0313637 A1    Oct. 17, 2019

(30) Foreign Application Priority Data
Dec. 23, 2016   (EP) .................... 16002735

(51) Int. Cl.
| | | |
|---|---|---|
| *A01N 25/28* | (2006.01) | |
| *A01N 25/10* | (2006.01) | |
| *A01N 25/04* | (2006.01) | |
| *A01N 25/26* | (2006.01) | |
| *A01N 37/34* | (2006.01) | |
| *A01N 43/40* | (2006.01) | |
| *A01N 43/54* | (2006.01) | |
| *A01N 43/647* | (2006.01) | |

(52) U.S. Cl.
CPC ............ *A01N 25/10* (2013.01); *A01N 25/04* (2013.01); *A01N 25/26* (2013.01); *A01N 25/28* (2013.01); *A01N 37/34* (2013.01); *A01N 43/40* (2013.01); *A01N 43/54* (2013.01); *A01N 43/647* (2013.01)

(58) Field of Classification Search
None
See application file for complete search history.

(56) References Cited

U.S. PATENT DOCUMENTS

| | | |
|---|---|---|
| 4,435,548 A | 3/1984 | Tomalia et al. |
| 4,568,737 A | 2/1986 | Tomalia et al. |
| 5,338,532 A | 8/1994 | Tomalia et al. |
| 2002/0161113 A1 | 10/2002 | Dvornic et al. |
| 2003/0069370 A1 | 4/2003 | Dvornic et al. |
| 2018/0334569 A9* | 11/2018 | Seelmann-Eggebert ............... C25D 3/12 |

FOREIGN PATENT DOCUMENTS

| | | |
|---|---|---|
| DE | 10351401 A1 | 6/2005 |
| DE | 10351401 A1 | 6/2005 |
| DE | 102004006304 A1 | 8/2005 |
| DE | 102004006304 A1 | 8/2005 |
| EP | 0071050 A1 | 2/1983 |
| EP | 0071050 A1 | 2/1983 |
| EP | 0115771 A2 | 8/1984 |
| EP | 0115771 A2 | 8/1984 |
| EP | 0234408 A2 | 9/1987 |
| EP | 0234408 A2 | 9/1987 |
| EP | 0802215 A1 | 10/1997 |
| EP | 0802215 A1 | 10/1997 |
| EP | 1273633 A2 | 1/2003 |
| EP | 1273633 A2 | 1/2003 |
| EP | 1474461 A1 | 11/2004 |
| EP | 1474461 B1 | 12/2007 |
| EP | 1389040 B1 | 5/2010 |
| RU | 2240002 C1 | 11/2004 |
| WO | 9314147 A1 | 7/1993 |
| WO | WO-93/14147 A1 | 7/1993 |
| WO | 9615097 A1 | 5/1996 |
| WO | WO-96/15097 A1 | 5/1996 |
| WO | 9635739 A1 | 11/1996 |
| WO | WO-96/35739 A1 | 11/1996 |

(Continued)

OTHER PUBLICATIONS

International Search Report for International Application No. PCT/EP2017/084061, dated Mar. 22, 2018, 4 pages.
Hobson et al., "Poly(amidoamine) hyperbranched systems: synthesis, structure and characterization", Polymer, Published Mar. 1999, pp. 1279-1297, vol. 40, No. 5.
European Search Report for EP Application No. 16002735.5, dated Jun. 30, 2016, 4 pages.
International Search Report for PCT Patent Application No. PCT/EP2017/084061, dated Mar. 22, 2018, 4 pages.

*Primary Examiner* — Brian Gulledge

(74) *Attorney, Agent, or Firm* — Armstrong Teasdale LLP

(57) ABSTRACT

Described herein is an aqueous composition including particles coated with at least one non-amphoteric, quaternizable polymer which is water soluble at 20° C., and at least one dispersing component, where the dispersing component includes a dispersing agent selected from an amphiphilic graft polymer based on water-soluble polyalkylene oxides (A) as a graft base and side chains formed by polymerization of a vinyl ester component (B), the polymer having an average of ≤1 graft site per 50 alkylene oxide units and a mean molar mass $M_w$ of from 3000 to 100 000.

14 Claims, No Drawings

(56) References Cited

FOREIGN PATENT DOCUMENTS

| WO | 2007138053 A1 | 12/2007 | |
|---|---|---|---|
| WO | WO-2007/138053 A1 | 12/2007 | |
| WO | WO-2007138053 A1 * | 12/2007 | ............ C08F 283/06 |
| WO | 2011110481 A1 | 9/2011 | |
| WO | WO-2011/110481 A1 | 9/2011 | |
| WO | WO-2011110481 A1 * | 9/2011 | ............. A01N 25/02 |
| WO | 2013068851 A2 | 5/2013 | |
| WO | WO-2013/068851 A2 | 5/2013 | |
| WO | 2016062880 A2 | 4/2016 | |
| WO | WO-2016/062880 A2 | 4/2016 | |
| WO | WO-2016062880 A2 * | 4/2016 | ............... C09C 3/10 |

\* cited by examiner

STABILIZATION OF PARTICLES COATED WITH NON-AMPHOTERIC, QUATERNIZABLE AND WATER-SOLUBLE POLYMERS USING A DISPERSING COMPONENT

CROSS-REFERENCE TO RELATED APPLICATIONS

This application is a U.S. National Phase Application of PCT/EP2017/084061, filed Dec. 21, 2017, which claims the benefit of priority to European Patent Application No. 16002735.5, filed Dec. 23, 2016, the entire contents of which are hereby incorporated by reference herein.

FIELD OF INVENTION

The present invention relates to the field of dispersing of surface-modified particles which are stabilized in aqueous suspensions.

Additional dispersing components have now been identified by the present invention that allow substantially improving the stability of the surface-modified particles in aqueous compositions. The aqueous compositions of the present invention are especially helpful for the preparation of agrochemical compositions like stabilized formulations of pesticides to be used in agricultural pest control.

In particular, the present invention is directed to aqueous compositions comprising particles coated with at least one non-amphoteric, quaternizable polymer which is water soluble at 20° C., and at least one dispersing component comprising a dispersing agent selected from an amphiphilic graft polymer based on water-soluble polyalkylene oxides (A) as a graft base and side chains formed by polymerization of a vinyl ester component (B), said polymer having an average of ≤1 graft site per 50 alkylene oxide units and mean molar masses $M_w$ of from 3000 to 100 000.

BACKGROUND

The coating of active ingredients, like for instance pesticides, with non-amphoteric, quaternizable polymers that are water soluble at 20° C. has been described in WO 2016/062880 A2. This approach allows the preparation of aqueous suspensions in which the active ingredient particles despite being often poorly soluble in such aqueous formulations show relatively homogenous formulation, rather reduced agglomeration and improved storage stability when compared with the naked particles lacking such additional polymeric coating.

However, it would be desirable to further stabilize the particles coated with at least one non-amphoteric, quaternizable polymer which is water soluble at 20° C. in order to even further improve stability characteristics of the coated particles with respect to less agglomeration of the particles, even higher homogeneity of the formulation and more controlled release of the active ingredient. The prolonged stability of the corresponding suspension concentrates also has high importance. In addition, when used in the field of pest control, one important property of the coated particles with their core of active ingredient is improved build-in rain fastness.

Accordingly, there is still the need to further improve the compositions comprising particles coated with at least one non-amphoteric, quaternizable polymer which is water soluble at 20° C. as disclosed in WO 2016/062880 A2.

DESCRIPTION

The present invention provides such improved aqueous compositions comprising coated particles in which the core of active ingredient shows reduced agglomeration, improved stability, particularly when formulated as suspension concentrate, excellent rain fastness and controlled release of the active ingredient after agricultural application.

The present invention relates to an aqueous composition comprising (a) particles coated with at least one non-amphoteric, quaternizable polymer which is water soluble at 20° C., and (b) at least one dispersing component comprising a dispersing agent selected from an amphiphilic graft polymer based on water-soluble polyalkylene oxides (A) as a graft base and side chains formed by polymerization of a vinyl ester component (B), said polymer having an average of ≤1 graft site per 50 alkylene oxide units and mean molar masses $M_w$ of from 3000 to 100 000.

In a preferred embodiment of the present invention, the amphiphilic graft polymer has a polydispersity $M_w/M_n$ of <3.

In another preferred embodiment of the present invention, the amphiphilic graft polymer comprises <10 wt % of polyvinyl ester (B) in ungrafted form.

In another preferred embodiment of the present invention, the amphiphilic graft polymer has (A) from 20 to 70 wt % of a water-soluble polyalkylene oxide as a graft base, and (B) side chains formed by free-radical polymerization of from 30 to 80 wt % of a vinyl ester component, composed of (B1) from 70 to 100 wt % of vinyl acetate and/or vinyl propionate, and (B2) from 0 to 30 wt % of a further ethylenically unsaturated monomer in the presence of (A).

In another preferred embodiment of the present invention, the amphiphilic graft polymer comprises from 25 to 60 wt % of the graft base (A) and from 40 to 75 wt % of the vinyl ester component (B).

In another preferred embodiment of the present invention, the vinyl ester component (B) of the amphiphilic graft polymer comprises from 70 to 100 wt % of vinyl acetate (B1) and from 0 to 30 wt % of a $C_1$ to $C_8$ alkyl acrylate (B2).

In another preferred embodiment of the present invention, the dispersing agent of the dispersing component is selected from an amphilic graft polymer obtained from the reaction of polyethylene oxide 6000 and vinyl acetate with a weight ratio of PEG 6000 to vinyl acetate of 40 to 60, optionally comprising further co-dispersing agents.

In another preferred embodiment of the present invention, the particles are selected from the group of organic compounds.

In another preferred embodiment of the present invention, the particles are selected from pesticides.

In another preferred embodiment of the present invention, the pesticide is selected from, Deltamethrin, Boscalid, Fluxapyroxad, Chlorothalonil, Epoxiconazole, Mefentrifluconazole, Strobilurins, like Azoxystrobin, Dimoxystrobin and combinations thereof.

In another preferred embodiment of the present invention, the non-amphoteric, quaternizable polymer water soluble at 20° C. is selected from the group consisting of polyvinylamines, polyvinylamidoamines, polyethyleneimines, polypropyleneimines, polyamidoamines or polyureaamines, cationic copolymers comprising the polymerisable monomers selected from vinylpyrrolidone, methacrylamide, vinyl imidazole, quaternized vinyl imidazole and combinations thereof, cationic copolymers comprising the cationic copolymers comprising the polymerizable monomers selected from vinylpyrrolidone and quaternized vinyl imidazole, cationic copolymers comprising the polymerizable monomers selected from vinylpyrrolidone and quaternized dimethylaminoethyl methacrylate (DMAEMA), cationic copolymers comprising the polymerizable monomers selected from vinyl caprolactam, vinylpyrrolidone and quaternized vinyl imidazole, and combinations of said polymers.

In another preferred embodiment of the present invention, the particles have a median particle size ($D_{50}$) in the range of 0.1 to 50 µm, more preferably 0.5 to 20 µm, even more preferably 1.0 to 10 µm, and most preferably 1.5 to 5.0 µm, and/or a median particle size ($D_{90}$) in the range of 0.1 to 50 µm, more preferably 0.5 to 20 µm, even more preferably 1.0 to 15 µm, and most preferably 1.5 to 10 µm, as measured with a Malvern Mastersizer 3000.

In another preferred embodiment of the present invention, the composition comprises 1.0 to 50.0 wt % of particles coated with at least one non-amphoteric, quaternizable polymer which is water soluble at 20° C.; and 0.1 to 15.0 wt % of at least one dispersing component comprising a dispersing agent selected from an amphiphilic graft polymer based on water-soluble polyalkylene oxides (A) as a graft base and side chains formed by polymerization of a vinyl ester component (B), said polymer having an average of ≤1 graft site per 50 alkylene oxide units and mean molar masses $M_w$ of from 3000 to 100 000 g/mol.

The present invention also relates to the use of the aqueous composition of the present invention for the preparation of an agrochemical, cosmetic or pharmaceutical formulation.

The present invention also relates to the use of at least one dispersing component for dispersing a non-amphoteric, quaternizable polymer which is water soluble at 20° C. in an aqueous composition.

The term "particle" as used herein relates to a particulate material that has only a limited extent or particle diameter. Preferred particles have a median particle size ($D_{50}$) in the range of 0.1 to 50 µm, more preferably 0.5 to 20 µm, even more preferably 1.0 to 10 µm, and most preferably 1.5 to 5.0 µm, and/or a median particle size ($D_{90}$) in the range of 0.1 to 50 µm, more preferably 0.5 to 20 µm, even more preferably 1.0 to 15 µm, and most preferably 1.5 to 10 µm, as measured with a Malvern Mastersizer 3000. Such median particle size distributions ($D_{50}$) and/or ($D_{90}$) can be preferably obtained after sedimentation for 24 h at RT after preparation, and/or, after storage for 14 days at −10 to 40° C., and/or, after storage for 14 days at 54° C.

Particles which are prepared by use of an aqueous composition having 0.01 to 30 wt %, preferably 0.1 to 15 wt %, and even more preferably 1 to 10 wt % polymer based on the total weight of the aqueous composition are especially preferred.

The particles preferably are organic particles, or particles comprising or even consisting of organic material or compounds.

Less preferred than organic particles are inorganic particles which are solid at room temperature (21° C.) like for instance those particles selected from the group of oxides, hydroxides, carbides, borides, sulfides, nitrides or combinations thereof. Amongst the inorganic particles, nitrides and carbides are preferred, especially boron nitride (BN), silicon carbide (SiC) and boron carbide ($B_4C$). Accordingly, non-metallic, inorganic particles are preferred inorganic particles.

Additionally or alternatively, diamond particles can also be used as inorganic particles of the present invention.

The particles of the present invention are preferably solid at room temperature (21° C.), and are even more preferably selected from pesticides.

The polymers used for coating the particles are non-amphoteric, quaternizable, water-soluble polymers.

The term "water-solubility at 20° C." of the polymers as used herein relates to polymers when at least 0.1 g of the corresponding polymer or the polymer mixture is soluble in 100 ml of water at 20° C.

The term "amphoteric" relates to polymers which have acidic and basic hydrophilic groups at the same time, particularly carboxy and/or sulfonic acid groups as the acidic groups and amino and/or amido groups as the basic groups. Amphoteric polymers can have acidic or basic properties depending on the ambient conditions.

According to this definition of the term "amphoteric", the present invention relates to non-amphoteric polymers which do not have at the same time acidic and basic groups, especially not at the same time carboxy and/or sulfonic acid groups as the acidic groups and amino and/or amido groups as the basic groups. The term "group" relates in this technical context predominantly to the side chains or side groups of the corresponding polymers.

The term "quaternizable polymer" relates to a polymer which has quaternizable amino or amido groups, especially quaternizable amino or amido groups as side groups, whereas a quaternizable amino or amido group or side group is characterized in that the latter group can be converted by alkylation in a quaternary amino or amido group.

However, this does not need to be understood in a way that the quaternizable amino or amido group in the quaternizable polymers of the present invention necessarily is already quaternized (alkylated).

Rather, the quaternizable polymers according to the present invention include quaternized polymers which are indeed quaternized, e.g. alkylated, preferably methylated, ethylated, propylated or butylated. Nonetheless, additionally, the present invention also includes those polymers, that are basically quaternizable based on the presence of a (quaternizable) amino and/or amido group while being not yet quaternized. Only the basic possibility for the alkylation at the nitrogen of the amino and/or amido group must be given in the polymers of the present invention.

The non-amphoteric, quaternizable and water-soluble at 20° C. polymers of the present invention include the following two larger sub-groups of preferred polymers: On the one hand polymeric amines including polyamines in the narrow sense and polyalkylenimines; and on the other hand cationic, non-amphoteric polymers which are water-soluble at 20° C.

a) Polymeric Amines (Polyamines, Polyalkyleneimines)

Suitable non-amphoteric, quaternizable polymers according to the present invention include in a first preferred embodiment polymeric amines, preferably polyamines in a narrow sense and polyalkyleneimines.

Preferred polyamines in the narrow sense preferably include the following polymers and groups of polymers: polyvinylamines, polyvinylamidoamines, polyamidoamines and polyureaamines. Preferred polyalkyleneimines include polyethyleneimines and polypropyleneimines.

Polymeric amines preferably have a mass average molecular weight (Mw) of 200 to 3 000 000, more preferably 200 to 2 000 000 g/mol. Generally, the content of amino groups is 5 to 35 mol/kg, more preferably 5 to 25 mol/kg, even more preferably 10 to 24 mol/kg. The structure of the polymers can be selected in a way that linear, branched or hyperbranched polymers, starpolymers or dendrimers are obtained.

Amongst the polyethylenimines and polypropyleneimines, linear, branched or hyperbranched polymers are preferred. Included herewith are homopolymers having 4, 5, 6, 10, 20, 35 and 100 repeating units.

Preferred polyethyleneimines are defined by the following formula (I)

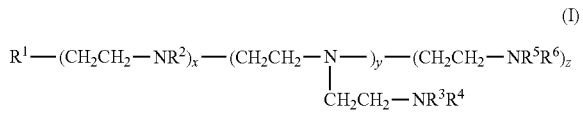

having an average molecular weight (Mw) of 200 to 2.000.000, whereas the residues $R^1$ to $R^6$ independently from each other are hydrogen, linear or branched $C_1$ to $C_{20}$ alkyl, alkoxy, polyoxyethylene, hydroxylated alkyl, alkylated carboxy, phosphonoalkyl, alkylated amino, $C_2$ to $C_{20}$ alkenyl, or $C_6$ to $C_{20}$ aryl, aryloxy, hydroxylated aryl, arylcarboxy or arylamino groups which are optionally further substituted; and whereas $R^4$ and $R^5$ can additionally represent further polyethyleneimine-type polymeric groups and x, y and z independently from each other define 0 or an integer; $R^1$ further can be a primary amino group.

The sum of x, y and z is selected to give an average molecular mass in the above-defined range. Preferred ranges for the average molecular weight ($M_w$) of the polyethyleneimines according to the general formula (I) are 250 to 500.00, preferably 300 to 100.000.

Preferred residues $R^1$ to $R^6$ are hydrogen, methyl, ethyl, carboxymethyl, carboxyethyl, phosphonomethyl, 2-hydroxy ethyl, 2-(2'-hydroxyethoxy)ethyl and 2-[2'-(2''-hydroxyethoxy)-ethoxy]ethyl and $R^1$ preferably is a primary amino group.

Suitable, non-limiting examples of commercially available polyethyleneimines include Lupasol® of BASF SE including Lupasol®FG, Lupasol®G20 water-free, Lupasol®PR8515, Lupasol®WF, Lupasol®FC, Lupasol®G20, Lupasol®G35, Lupasol®G100, Lupasol®HF, Lupasol®P, Lupasol®PS, Lupasol®SK, Lupasol®SNA.

Linear and branched polyethyleneimines are also summarized in Römpp, Chemisches Lexikon, Online-Version 2004, Georg Thieme-Verlag and the additional literature cited therein.

Amongst the polyvinylamines and the polyvinylamidoamines, linear polyvinylamines are preferred. Polyvinylamines are generally known and for instance described in EP 0 071 050 A1. Accordingly, all polyvinylamines and polyvinylamidoamines as well as their preparation and relevant methods of characterization according to EP 0 071 050 A1 are herein incorporated by reference and considered to be part of the present invention.

Suitable, non-limiting examples of commercially available linear polyvinyl amines include Lupamin® and Catiofast® by BASF SE. Preferred commercial products are Lupamin®9095, Lupamin®9050, Lupamin®9030, Lupamin®9010, Lupamin®5095, and Lupamin®1595.

Preferred polyvinylamines and polyvinylamidoamines according to the present invention are polyallylamine, poly (diallyldimethylammonium chloride), polyvinylformamide, polyvinylpyrrolione, polyvinylacetamide, polyvinylmethylformamide, polyvinylmethylacetamide, poly(dimethylaminopropylmethacrylamide), poly(dimethylaminoethylacrylate), poly(diethylaminoethylacrylate), poly (acryloylethyltrimethylammonium chloride), poly (acrylamidopropyltrimethylammonium chloride), poly (methacrylamidopropyltrimethylammonium chloride), polyacrylamide, poly(vinylpyridine), hexadimethrine bromide, poly(dimethylamine-co-epichlorhydrine), poly(dimethylamine-coepichlorhydrine-co-ethylendiamine), poly (amidoaminepichlorhydrine) or copolymers thereof, N-vinylformamide, allylamine, diallyldimethylammonium chloride, N-vinylacetamide, N-vinylpyrrolidone, N-methyl-N-vinylformamide, N-methyl-N-vinylacetamide, dimethylaminopropylmethacrylamide, dimethylaminoethylacrylate, diethylaminoethylacrylate, acryloylethyltrimethylammonium chloride or methacrylamidopropyltrimethylammonium chloride contained in copolymerized form and optionally in a forked shape. Additionally, the polymers as mentioned can be used in cationic or anionic form, or as the salts thereof. Non-ionic or cationic polyvinylformamides, polyvinylamine, polyacrylamide and poly (diallyldimethylammonium chloride) are preferred. Especially preferred are cationic polyvinylformamide or polyvinylamine.

Especially preferred is the polyvinylamine according to the general formula (II)

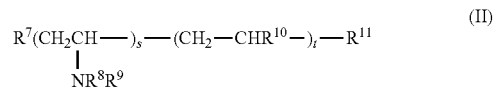

having an average molecular weight by mass (Mw) of 200 to 2.000.000, the residues $R^7$ to $R^{11}$ independently of each other being hydrogen, linear or branched $C_1$- to $C_{20}$-alkyl-, -alkoxy-, -polyoxyethylene-, -hydroxyalkyl-, -(alkyl)carboxy-, -phosphonoalkyl-, -alkylamino residues, $C_2$- to $C_{20}$-alkenyl residues or $C_6$- to $C_{20}$-aryl-, -aryloxy-, -hydroxyaryl-, -arylcarboxy-, or -arylamino residues, which are optionally further substituted, and additionally representing formamidyl-, pyrrolidonyl- or imidazolyl residue, s representing an integer and t=0 or an integer, whereas said polyvinylamine can be quaternizable at the tertiary and/or free primary and/or secondary N-atoms present in the compounds according to formula (II).

The sum of s and t has to be selected in a way that the average molecular weight is in the given range. Preferred ranges for the average molecular weight (Mw) of the polyvinylamines are 500 to 500.000, preferably 800 to 50.000.

Preferred definitions for residues $R^7$ to $R^{11}$ are also those, which are given above for $R^1$ to $R^6$ of the general formula (I).

Additional polymers included by the present invention are linear polyamidoamines as well as branched or hyperbranched polyamidoamines, like for instance described in U.S. Pat. No. 4,435,548, EP 0 115 771, EP 0 234 408, EP 0 802 215, in L. J. Hobson and W. J. Feast, Polymer 40 (1999), 1279-1297 or in H.-B. Mekelburger, W. Jaworek and F. Vögtle, Angew. Chemie 1992, 104, no. 12, 1609-1614.

Preferred polyamidoamines have an average molecular weight ($M_w$) of 500 to 1.000.000. They are available for instance by reacting $C_2$- to $C_{10}$-dicarboxylic acids or tricarboxylic acids with poly($C_2$- to $C_4$-alkylene)polyamines having 2 to 20 basic nitrogen atoms per molecule, having a suitable number of primary and/or secondary amino groups which are capable of forming amid or ester bonds with the carboxylic acid.

Especially preferred ranges for the average molecular weight ($M_w$) of the polyamidoamines are 800 to 800.00, particularly 1000 to 100.000.

As a further class of polymers, the present invention relates to polyureaamines containing amino groups. Preferred polyureaamines comprise branched or hyperbranched amino groups like for instance disclosed in EP 1 474 461, DE 10 351 401 and DE 10 2004 006 304 as well as in EP 1 273 633, US 2002/0161113 or US 2003/0069370.

Dendrimers or dendrimer-type amines or their precursors are, for example, N,N,N',N'-tetraaminopropylalkylendiamine, wherein as alkylene unit preferably the ethylene or butylene unit is selected, wherein these amines generally are referred to as N6-amines, as measured by the number of nitrogen atoms, and the dendrimeric amines like N14-, N30-, N62- and N128-amine prepared therefrom by aminopropylation. These amines have an ethylene diamine or butylene diamine backbone, whose hydrogen atoms at the nitrogen are substituted by amino (n-propyl) residues. The terminal amino groups can in turn be substituted by corresponding aminopropyl groups (N14-amine), etc. Methods for the preparation of these amines are described in WO 96/15097, starting from ethylene diamine, and are herewith incorporated by reference. Also preferred examples of these amines are the corresponding N-amines, which are prepared starting from butylene diamine instead of ethylene diamine as described above. The latter compounds are described in WO 93/14147 which are also herein incorporated by reference.

Other dendrimers or dendrimer-type amines can be constructed, for example, based on polyamide chemistry, for example as described in U.S. Pat. No. 4,568,737 or 5,338,532.

Another class of nitrogen atom-containing polymers are amino group-containing star polymers, for example as described in the WO 96/35739.

b) Cationic, Non-Amphoteric and Quaternizable Polymers

Other suitable non-amphoteric and quaternizable polymers of the present invention include in a second preferred embodiment the following cationic, non-amphoteric and quaternizable polymers:

Copolymers comprising the polymerizable monomers of vinylpyrrolidone, methacrylamide, vinylimidazole and quaternized vinylimidazole. Such polymers are known to the skilled person and include products such as Polyquaternium-68 (e.g. Luviquat® Supreme or Luviquat® Supreme AT 1 from BASF SE).

Copolymers comprising the polymerizable monomers vinylpyrrolidone and quaternized vinylimidazole. Such polymers are known to the skilled person and include products such as Polyquaternium-16 and Polyquaternium-44 (e.g. Luviquat® HM 552, Luviquat® Style, Luviquat® Style AT 1, Luviquat® FC 370, Luviquat® FC 550, Luviquat® Excellence, Luviquat® UltraCare or Luviquat® Ultracare AT 1 from BASF SE).

Copolymers comprising the polymerizable monomers vinylpyrrolidone and quaternized dimethylaminoethylmethacrylate (DMAEMA). Such polymers are known to the skilled person and include products such as Polyquaternium-11 (e.g. Luviquat® PQ 11 PN or Luviquat® PQ 11 AT 1 from BASF SE).

Copolymers comprising the polymerizable monomers vinylcaprolactam, vinylpyrrolidone and quaternized vinylimidazole. Such polymers are known to the skilled person and include products such as Polyquaternium-46 (e.g. Luviquat® Hold and Luviquat® Hold AT 2 from BASF SE).

The non-amphoteric, quaternizable polymers of the present invention can optionally be obtained by mixtures of polymers selected from the first and second preferred embodiment of the present invention.

The preparation of the particles of the present invention comprising at the surface a coating of a non-amphoteric, quaternizable polymer which is water-soluble at 20° C. includes contacting a particle in an aqueous medium with at least one of the polymers of the present invention. Accordingly, the solid particles are contacted with the polymer in an aqueous medium, whereas the polymer is provided in the aqueous medium and this polymer solution is mixed with the solid particles.

Preferably, the suspension comprising the particles and the non-ampholytic, quaternizable polymer water-soluble at 20° C. is subsequently stirred allowing the polymer to attach to the surface of the particles. Preferably, the polymer attaches to the surface of the particles based on physical interaction. That is, in a preferred embodiment, no chemical bond between the polymer and the particle is formed. Stirring of the mixture is preferably carried out over a period of at least a couple of hours, for instance for at least 1 h, 2 h, 5 h, 10 h or 24 h. Higher amounts of polymer, e.g. PEI, like an access of polymer, e.g. PEI, allow limiting the time of stirring. Especially preferred for achieving a very high extent of surface modification of the particles by the polymer is to stir for at least 2 h, or even more preferably for at least 5 h, especially when an access of polymer, e.g. PEI is used.

After the treatment, particles are separated from the solution, for instance by filtering or centrifuging. The particles are subsequently optionally washed with water until the washing solution has neutral pH value and dried. Alternatively, the particles are left in the aqueous polymeric dispersion and can be directly used further.

The treatment of the solid particles with the solution of polymer is preferably carried out at a temperature of 10 to 90° C., preferably 15 to 35° C. and even more preferably 18 to 30° C.

In the present invention, the particles coated with at least one non-amphoteric, quaternizable polymer which is water soluble at 20° C. are additionally stabilized with a special dispersing component. Accordingly, the present invention relates to compositions comprising the combination of particles coated with at least one non-amphoteric, quaternizable polymer which is water soluble at 20° C. and at least one dispersing component comprising a dispersing agent.

The dispersing agent suitable for stabilizing the at least one non-amphoteric, quaternizable polymer which is water soluble at 20° C. is an amphiphilic graft polymer-type dispersing agent.

Such amphiphilic graft polymer has been described in WO 2007/138053 A1, which is herein incorporated by reference, particularly with respect to the structure of the dispersing agent and its preparation.

The inventive graft polymers are characterized by their low degree of branching (degree of grafting). They have, on average, based on the reaction mixture obtained, not more than 1 graft site, preferably not more than 0.6 graft site, more preferably not more than 0.5 graft site and most preferably not more than 0.4 graft site per 50 alkylene oxide units. They comprise, on average, based on the reaction mixture obtained, preferably at least 0.05, in particular at least 0.1 graft site per 50 alkylene oxide units. The degree of branching can be determined, for example, by means of $^{13}$C NMR spectroscopy from the integrals of the signals of the graft sites and the —CH$_2$— groups of the polyalkylene oxide.

In accordance with their low degree of branching, the molar ratio of grafted to ungrafted alkylene oxide units in the inventive graft polymers is from 0.002 to 0.05, preferably from 0.002 to 0.035, more preferably from 0.003 to 0.025 and most preferably from 0.004 to 0.02.

The inventive graft polymers feature a narrow molar mass distribution and hence a polydispersity $M_w/M_n$ of generally ≤3, preferably ≤2.5 and more preferably ≤2.3. Most preferably, their polydispersity $M_w/M_n$ is in the range from 1.5 to 2.2. The polydispersity of the graft polymers can be determined, for example, by gel permeation chromatography using narrow-distribution polymethyl methacrylates as the standard.

The mean molecular weight $M_w$ of the inventive graft polymers is from 3000 to 100 000, preferably from 6000 to 45 000 and more preferably from 8000 to 30 000.

Owing to their low degree of branching and their low polydispersity, the amphiphilic character and the block polymer structure of the inventive graft polymers is particularly marked.

The inventive graft polymers also have a low content of ungrafted polyvinyl ester (B). In general, they comprise ≤10 wt %, preferably ≤7.5 wt % and more preferably ≤5 wt % of ungrafted polyvinyl ester (B).

Owing to the low content of ungrafted polyvinyl ester and the balanced ratio of components (A) and (B), the inventive graft polymers are soluble in water or in water/alcohol mixtures (for example a 25 wt % solution of diethylene glycol monobutyl ether in water). They have pronounced, low cloud points which, for the graft polymers soluble in water at up to 50° C., are generally ≤95° C., preferably ≤85° C. and more preferably ≤75° C., and, for the other graft polymers in 25 wt % diethylene glycol monobutyl ether, generally ≤90° C., preferably from 45 to 85° C.

The inventive amphiphilic graft polymers have preferably (A) from 20 to 70 wt % of a water-soluble polyalkylene oxide as a graft base and (B) side chains formed by free-radical polymerization of from 30 to 80 wt % of a vinyl ester component, based on the total weight of the amphiphilic graft polymer, wherein the vinyl ester component (B) is composed of (B1) from 70 to 100 wt % of vinyl acetate and/or vinyl propionate and (B2) from 0 to 30 wt % of a further ethylenically unsaturated monomer, based on the total amount of the vinyl ester component (B).

More preferably, they comprise from 25 to 60 wt % of the graft base (A) and from 40 to 75 wt % of the polyvinyl ester component (B).

Water-soluble polyalkylene oxides suitable for forming the graft base (A) are in principle all polymers based on $C_2$ to $C_4$-alkylene oxides which comprise at least 50 wt %, preferably at least 60 wt %, more preferably at least 75 wt % of ethylene oxide in copolymerized form.

The polyalkylene oxides (A) preferably have a low polydispersity $M_w/M_n$. Their polydispersity is preferably ≤1.5.

The polyalkylene oxides (A) may be the corresponding polyalkylene glycols in free form, i.e. with OH end groups, but they may also be capped at one or both end groups. Suitable end groups are, for example, $C_1$ to $C_{25}$-alkyl, phenyl and $C_1$-$C_{14}$-alkylphenyl groups.

Specific examples of particularly suitable polyalkylene oxides (A) include:

(A1) polyethylene glycols which may be capped at one or both end groups, especially by C to $C_{25}$ alkyl groups, but are preferably not etherified, and have mean molar masses $M_n$ of preferably from 1500 to 20 000, more preferably from 2500 to 15 000;

(A2) copolymers of ethylene oxide and propylene oxide and/or butylene oxide with an ethylene oxide content of at least 50 wt %, which may likewise be capped at one or both end groups, especially by $C_1$ to $C_{25}$-alkyl groups, but are preferably not etherified, and have mean molar masses $M_n$ of preferably from 1500 to 20 000, more preferably from 2500 to 15 000;

(A3) chain-extended products having mean molar masses of in particular from 2500 to 20 000, which are obtainable by reacting polyethylene glycols (A1) having mean molar masses $M_n$ of from 200 to 5000 or copolymers (A2) having mean molar masses $M_n$ of from 200 to 5000 with $C_2$ to $C_{12}$ dicarboxylic acids or -dicarboxylic esters or $C_6$ to $C_{18}$ diisocyanates.

Preferred graft bases (A) are the polyethylene glycols (A1).

The side chains of the inventive graft polymers are formed by polymerization of a vinyl ester component (B) in the presence of the graft base (A).

The vinyl ester component (B) may consist advantageously of (B1) vinyl acetate or vinyl propionate or of mixtures of vinyl acetate and vinyl propionate, particular preference being given to vinyl acetate as the vinyl ester component (B).

However, the side chains of the graft polymer can also be formed by copolymerizing vinyl acetate and/or vinyl propionate (B1) and a further ethylenically unsaturated monomer (B2). The fraction of monomer (B2) in the vinyl ester component (B) may be up to 30 wt %, which corresponds to content in the graft polymer of (B2) of 24 wt %.

Suitable comonomers (B2) are, for example, less preferably, monoethylenically unsaturated carboxylic acids and dicarboxylic acids and anhydrides thereof, or, more preferably, their nonacidic derivatives, such as esters, amides and the like, and styrene. It is of course also possible to use mixtures of different comonomers.

Specific examples include: (meth)acrylic acid, $C_1$ to $C_{12}$ alkyl and hydroxy-$C_2$-$C_{12}$-alkyl esters of (meth)acrylic acid, (meth)acrylamide, N—$C_1$-$C_{12}$-alkyl(meth)acrylamide, N,N-di($C_1$-$C_6$-alkyl)(meth)acrylamide, maleic acid, maleic anhydride and mono($C_1$-$C_{12}$-alkyl)esters of maleic acid.

Preferred monomers (B2) are the $C_1$-$C_8$-alkyl esters of (meth)acrylic acid and hydroxyethyl acrylate, particular preference being given to the $C_1$-$C_4$-alkyl esters of (meth) acrylic acid.

Very particularly preferred monomers (B2) are methyl acrylate, ethyl acrylate and in particular n-butyl acrylate.

When the inventive graft polymers comprise the monomers (B2) as a constituent of the vinyl ester component (B), the content of graft polymers in (B2) is preferably from 0.5 to 20 wt %, more preferably from 1 to 15 wt % and most preferably from 2 to 10 wt %.

In another preferred embodiment of the present invention, the dispersing agent of the present invention is a graft copolymer obtained by grafting a polyalkylene oxide of number average molecular weight of 2000 to 100 000 with vinyl acetate, which is optionally partially saponified, in a weight ratio of polyalkylene oxide to vinyl acetate of 1:0.2 to 1:10. The vinyl acetate optionally is saponified to an extent of up to 15%. The polyalkylene oxide preferably contains units of ethylene oxide, propylene oxide and/or butylene oxide. Polyethylene oxide is the most preferred polyalkylene oxide.

The polyalkylene oxide has a number average molecular weight of 4000 to 50 000, the weight ratio of polyalkylene oxide to vinyl acetate preferably is from 1:0.5 to 1:6. Especially preferred are graft polymers derived from polyethylene oxide of molecular weight 2000 to 50 000 and having a weight ratio of polyethylene oxide to vinyl acetate of from 1:0.5 to 1:6.

Another preferred dispersing agent of the present invention is an amphiphilic graft polymer obtained from the reaction of polyethylene oxide 6000 (equivalent to about 136 ethylene oxide units) with vinyl acetate with a weight ratio of PEG 6000 to vinyl acetate of 40 to 60, or about 3 parts by weight of vinyl acetate units per 1 part by weight of polyethylene oxide.

The dispersing component of the present invention comprising the dispersing agent of the present invention can optionally comprise further co-dispersing agents.

The combined total amount of dispersing agents and the optional co-dispersing agents of the dispersing component of the inventive compositions comprising the coated particles and the dispersing component preferably is in the range of 0.1 to 15.0 wt %, preferably 0.5 to 10.0 wt %, more preferably 1.0 to 5.0 wt %, and even more preferably 2.0 to 3.0 wt % based on the total weight of the composition.

Regarding the total dispersing component representing the total amount of dispersing agent and the optional co-dispersing agent, the at least one dispersing agent is preferably present in amount of 60 to 97 wt %, more preferably 70 to 95 wt %, and most preferably 80 to 90 wt %, based on the total amount of dispersing agents and co-dispersing agents, ie the total dispersing component. The at least one optional co-dispersing agent preferably is present in an amount of 3 to 40 wt %, more preferably 5 to 30 wt %, and most preferably 10 to 20 wt %, based on the total amount of dispersing agents and co-dispersing agents, ie the total dispersing component.

Optional conventional co-dispersing agents also include adjuvants, wetters, tackifiers, emulsifiers like alkali metal, alkaline earth metal and ammonium salts of aromatic sulfonic acids, such as ligninsulfonic acid (e.g. Borresperse®-types, Borregard, Norway), phenolsulfonic acid, naphthalenesulfonic acid (e.g. Morwet®-types, Akzo Nobel, U.S.A.), dibutylnaphthalene-sulfonic acid (e.g. Nekal®-types, BASF, Germany), and fatty acids, alkylsulfonates, alkyl-arylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (e.g. Mowiol®-types, Clariant, Switzerland), polyalkoxylates, polyvinylamines (e.g. Lupamin®-types, BASF SE, Germany), polyvinylpyrrolidone and the copolymers thereof.

Further optional co-dispersing agents that can be used in the dispersing component of the present invention in addition to the dispersing agent of the present invention are non-ionic alcohol alkoxylates, like non-ionic alcohol ethoxylates or alkoxylates, preferably non-ionic branched alcohol ethoxylates. The degree of ethoxylation can preferably be from 4 to 14. It is further preferred that such co-dispersing agents are selected from $C_{10}$-Guerbet alcohol ethoxylates according to the general formula $RO(CH_2CH_2O)_xH$ with $R=C_{10}H_{21}$ and x=4 to 14. The skilled person will be familiar with $C_{10}$-Guerbet alcohols that can be obtained by known preparation processes. Such $C_{10}$-Guerbet alcohol alkoxylates can be present in an amount of 5 to 30 wt %, more preferably 10 to 20 wt %, based on the total amount of combined dispersing agents and co-dispersing agents in the aqueous compositions of the present invention, ie based on the total amount of dispersing component. Optional non-ionic co-dispersing agents which are based on ethoxylated branched $C_{10}$-Guerbet alcohols are known to those skilled in the art and include commercially available products such as Lutensol® XL and XP series (BASF SE).

Additional or alternative co-dispersing agents can optionally include dialkylene glycols, preferably diethylene or dipropylene glycols, optionally being present in limited amounts of 1 to 15 wt %, preferably 3 to 10 wt %, based on the total amount of dispersing component, ie the total amount of the dispersing agents and co-dispersing agents in the aqueous compositions of the present invention.

The use of pre-mixtures of dispersing and co-dispersing agents as the dispersing component may be suitable to be used in the current invention. Suitable, non-limiting examples of commercially available pre-mixtures include pre-mixtures of the Agnique® series, such as Agnique® CP 72 L (BASF SE). Further suitable conventional surfactants (especially for agrochemical compositions comprising glyphosate) are alkoxylated $C_{4-22}$-alkylamines, such as ethoxylated tallow amine (POEA) and the surfactants disclosed in EP1389040 (e.g. those in Examples 1 to 14).

One preferred mixture of a dispersing component of at least one dispersing agent and at least one co-dispersing agent comprises the following components based on the total amount of dispersing component, ie the total amount of dispersing agents and co-dispersing agents:

a) an amphilic graft polymer obtained from the reaction of polyethylene oxide 6000 (equivalent to about 136 ethylene oxide units) with vinyl acetate with a weight ratio of PEG 6000 to vinyl acetate of 40 to 60, or about 3 parts by weight of vinyl acetate units per 1 part by weight of polyethylene oxide, preferably in an amount of 65 to 95 wt %, more preferably 75 to 90 wt %;

b) a $C_{10}$-Guerbet alcohol ethoxylate according to the general formula $RO(CH_2CH_2O)_xH$ with $R=C_{10}H_{21}$ and x=4 to 14, preferably present in an amount of 5 to 30 wt %, more preferably 10 to 20 wt %; and optionally, c) a dipropylene glycol, preferably present in an amount of 1 to 15 wt %, preferably 3 to 10 wt %.

The inventive graft polymers are advantageously obtainable by the process which is likewise in accordance with the invention, by polymerizing a vinyl ester component (B) composed of vinyl acetate and/or vinyl propionate (B1) and, if desired, a further ethylenically unsaturated monomer (B2), in the presence of a water-soluble polyalkylene oxide (A), a free radical-forming initiator (C) and, if desired, up to 40 wt %, based on the sum of components (A), (B) and (C), of an organic solvent (D), at a mean polymerization temperature at which the initiator (C) has a decomposition half-life of from 40 to 500 min, in such a way that the fraction of unconverted graft monomer (B) and initiator (C) in the reaction mixture is constantly kept in a quantitative deficiency relative to the polyalkylene oxide (A).

In this process, preference is given to using from 30 to 80 wt % of a vinyl ester component (B) composed of (B1) from 70 to 100 wt % of vinyl acetate and/or vinyl propionate and (B2) from 0 to 30 wt % of a further ethylenically unsaturated monomer and from 20 to 70 wt % of a water-soluble polyalkylene oxide (A) of mean molar mass $M_n$ of from 1500 to 20 000.

The amount of initiator (C) is preferably from 0.2 to 5 wt %, in particular from 0.5 to 3.5 wt %, based in each case on component (B).

For the process according to the invention, it is essential that the steady-state concentration of radicals present at the mean polymerization temperature is substantially constant and the graft monomer (B) is present in the reaction mixture constantly only in low concentration (for example of not more than 5 wt %). This allows the reaction to be controlled, and graft polymers can be prepared in a controlled manner with the desired low degree of branching and the desired low polydispersity.

The term "mean polymerization temperature" is intended to mean here that, although the process is substantially isothermal, there may, owing to the exothermicity of the reaction, be temperature variations which are preferably kept within the range of +/−10° C., more preferably in the range of +/−5° C.

According to the invention, the free radical-forming initiator (C) at the mean polymerization temperature should have a decomposition half-life of from 40 to 500 min, preferably from 50 to 400 min and more preferably from 60 to 300 min.

According to the invention, the initiator (C) and the graft monomer (B) are advantageously added in such a way that a low and substantially constant concentration of undecomposed initiator and graft monomer (B) is present in the reaction mixture. The proportion of undecomposed initiator in the overall reaction mixture is preferably ≤15 wt %, in particular ≤10 wt %, based on the total amount of initiator metered in during the monomer addition.

The mean polymerization temperature is appropriately in the range from 50 to 140° C., preferably from 60 to 120° C. and more preferably from 65 to 110° C.

Examples of suitable initiators (C) whose decomposition half-life in the temperature range from 50 to 140° C. is from 20 to 500 min are:

- O—$C_2$-$C_{12}$-acylated derivatives of tert-$C_4$-$C_{12}$-alkyl hydroperoxides and tert-($C_9$-$C_{12}$-aralkyl) hydroperoxides, such as tert-butyl peroxyacetate, tert-butyl monoperoxy-maleate, tert-butyl peroxyisobutyrate, tert-butyl peroxypivalate, tert-butyl peroxyneoheptanoate, tert-butyl peroxy-2-ethylhexanoate, tert-butyl peroxy-3,5,5-trimethylhexanoate, tert-butyl peroxyneodecanoate, tert-amyl peroxypivalate, tert-amyl peroxy-2-ethylhexanoate, tert-amyl peroxyneodecanoate, 1,1,3,3-tetramethylbutyl peroxyneodecanoate, cumyl peroxyneodecanoate, tert-butyl peroxybenzoate, tert-amyl peroxybenzoate and di-tert-butyl diperoxyphthalate;
- di-O—$C_4$-$C_{12}$-acylated derivatives of tert-$C_8$-$C_{14}$-alkylene bisperoxides, such as 2,5-dimethyl-2,5-di(2-ethylhexanoylperoxy) hexane, 2,5-dimethyl-2,5-di(benzoylperoxy)hexane and 1,3-di(2-neodecanoylperoxyisopropyl) benzene;
- di($C_2$-$C_{12}$-alkanoyl) and dibenzoyl peroxides, such as diacetyl peroxide, dipropionyl peroxide, disuccinyl peroxide, dicapryloyl peroxide, di(3,5,5-trimethylhexanoyl) peroxide, didecanoyl peroxide, dilauroyl peroxide, dibenzoyl peroxide, di(4-methylbenzoyl) peroxide, di(4-chlorobenzoyl) peroxide and di(2,4-dichlorobenzoyl) peroxide;
- tert-$C_4$-$C_5$-alkyl peroxy($C_4$-$C_{12}$-alkyl) carbonates, such as tert-amyl peroxy(2-ethylhexyl) carbonate;
- di($C_2$-$C_{12}$-alkyl) peroxydicarbonates, such as di(n-butyl) peroxydicarbonate and di(2-ethylhexyl) peroxydicarbonate.

Depending on the mean polymerization temperature, examples of particularly suitable initiators (C) are:

at a mean polymerization temperature of from 50 to 60° C.:
tert-butyl peroxyneoheptanoate, tert-butyl peroxyneodecanoate, tert-amyl peroxypivalate, tert-amyl peroxyneodecanoate, 1,1,3,3-tetramethylbutyl peroxyneodecanoate, cumyl peroxyneodecanoate, 1,3-di(2-neodecanoyl peroxyisopropyl) benzene, di(n-butyl) peroxydicarbonate and di(2-ethylhexyl) peroxydicarbonate;

at mean polymerization temperature of from 60 to 70° C.:
tert-butyl peroxypivalate, tert-butyl peroxyneoheptanoate, tert-butyl peroxyneodecanoate, tert-amyl peroxypivalate and di(2,4-dichlorobenzoyl) peroxide;

at a mean polymerization temperature of from 70 to 80° C.:
tert-butyl peroxypivalate, tert-butyl peroxyneoheptanoate, tert-amyl peroxypivalate, dipropionyl peroxide, dicapryloyl peroxide, didecanoyl peroxide, dilauroyl peroxide, di(2,4-dichlorobenzoyl) peroxide and 2,5-dimethyl [-2,5-di(2-ethylhexanoyiperoxy) hexane;

at a mean polymerization temperature of from 80 to 90° C.:
tert-butyl peroxyisobutyrate, tert-butyl peroxy-2-ethylhexanoate, tert-amyl peroxy-2-ethylhexanoate, dipropionyl peroxide, dicapryloyl peroxide, didecanoyl peroxide, dilauroyl peroxide, di(3,5,5-trimethylhexanoyl) peroxide, dibenzoyl peroxide and di(4-methylbenzoyl) peroxide;

at a mean polymerization temperature of from 90 to 100° C.:
tert-butyl peroxyisobutyrate, tert-butyl peroxy-2-ethylhexanoate, tert-butyl monoperoxy-maleate, tert-amyl peroxy-2-ethylhexanoate, dibenzoyl peroxide and di(4-methylbenzoyl) peroxide;

at a mean polymerization temperature of from 100 to 110° C.:
tert-butyl monoperoxymaleate, tert-butyl peroxyisobutyrate and tert-amyl peroxy(2-ethylhexyl) carbonate;

at a mean polymerization temperature of from 110 to 120° C.:
tert-butyl monoperoxymaleate, tert-butyl peroxy-3,5.5-trimethylhexanoate and tert-amyl peroxy(2-ethylhexyl) carbonate.

Preferred initiators (C) are O—$C_4$-$C_{12}$-acylated derivatives of tert-$C_4$-$C_5$-alkyl hydroperoxides, particular preference being given to tert-butyl peroxypivalate and tert-butyl peroxy-2-ethylhexanoate.

Particularly advantageous polymerization conditions can be established effortlessly by precise adjustment of initiator (C) and polymerization temperature. For instance, the preferred mean polymerization temperature in the case of use of tert-butyl peroxypivalate is from 60 to 80° C., and, in the case of tert-butyl peroxy-2-ethylhexanoate, from 80 to 100° C.

The inventive polymerization reaction can be carried out in the presence of small amounts of an organic solvent (D).

It is of course also possible to use mixtures of different solvents (D). Preference is given to using water-soluble or water-miscible solvents.

When a solvent (D) is used as a diluent, generally from 1 to 40 wt %, preferably from 1 to 35 wt %, more preferably from 1.5 to 30 wt %, most preferably from 2 to 25 wt %, based in each case on the sum of the components (A), (B) and (C), are used.

Examples of suitable solvents (D) include:
monohydric alcohols, preferably aliphatic $C_1$-$C_{16}$-alcohols, more preferably aliphatic $C_2$-$C_{12}$-alcohols, most preferably $C_2$-$C_4$-alcohols, such as ethanol, propanol, isopropanol, butanol, sec-butanol and tert-butanol;
polyhydric alcohols, preferably $C_2$-$C_{10}$-diols, more preferably $C_2$-$C_6$-diols, most preferably $C_2$-$C_4$-alkylene glycols, such as ethylene glycol and propylene glycol;
alkylene glycol ethers, preferably alkylene glycol mono ($C_1$-$C_{12}$-alkyl) ethers and alkylene glycol di($C_1$-$C_6$-alkyl) ethers, more preferably alkylene glycol mono- and di($C_1$-$C_2$-alkyl) ethers, most preferably alkylene glycol mono($C_1$-$C_2$-alkyl) ethers, such as ethylene glycol monomethyl and -ethyl ether and propylene glycol mono-methyl and -ethyl ether;
polyalkylene glycols, preferably poly($C_2$-$C_4$-alkylene) glycols having 2-20 $C_2$-$C_4$-alkylene glycol units, more preferably polyethylene glycols having 2-20 ethylene glycol units and polypropylene glycols having 2-10 propylene glycol units, most preferably polyethylene glycols having 2-15 ethylene glycol units and polypropylene glycols having 2-4 propylene glycol units, such as diethylene glycol, triethylene glycol, dipropylene glycol and tripropylene glycol;
polyalkylene glycol monoethers, preferably poly($C_2$-$C_4$-alkylene) glycol mono ($C_1$-$C_{25}$-alkyl) ethers having 2-20 alkylene glycol units, more preferably poly($C_2$-$C_4$-alkylene) glycol mono($C_1$-$C_{20}$-alkyl) ethers having 2-20 alkylene glycol units, most preferably poly($C_2$-$C_3$-alkylene) glycol mono($C_1$-$C_{16}$-alkyl) ethers having 3-20 alkylene glycol units;
carboxylic esters, preferably $C_1$-$C_8$-alkyl esters of $C_1$-$C_6$-carboxylic acids, more preferably $C_1$-$C_4$-alkyl esters of $C_1$-$C_3$-carboxylic acids, most preferably $C_2$-$C_4$-alkyl esters of $C_2$-$C_3$-carboxylic acids, such as ethyl acetate and ethyl propionate;
aliphatic ketones which preferably have from 3 to 10 carbon atoms, such as acetone, methyl ethyl ketone, diethyl ketone and cyclohexanone;
cyclic ethers, in particular tetrahydrofuran and dioxane.

The solvents (D) are advantageously those solvents, which are also used to formulate the inventive graft polymers for use (for example in washing and cleaning compositions) and can therefore remain in the polymerization product.

Preferred examples of these solvents are polyethylene glycols having 2-15 ethylene glycol units, polypropylene glycols having 2-6 propylene glycol units and in particular alkoxylation products of $C_6$-$C_8$-alcohols (alkylene glycol monoalkyl ethers and polyalkylene glycol monoalkyl ethers).

Particular preference is given here to alkoxylation products of $C_8$-$C_{16}$-alcohols with a high degree of branching, which allow the formulation of polymer mixtures which are free-flowing at 40-70° C. and have a very low polymer content at comparatively low viscosity. The branching may be present in the alkyl chain of the alcohol and/or in the polyalkoxylate moiety (copolymerization of at least one propylene oxide, butylene oxide or isobutylene oxide unit).

Particularly suitable examples of these alkoxylation products are 2-ethylhexanol or 2-propylheptanol alkoxylated with 1-15 mol of ethylene oxide, $C_{13}$/$C_{15}$ oxo alcohol or $C_{12}$/$C_{14}$ or $C_{16}$/$C_{18}$ fatty alcohol alkoxylated with 1-15 mol of ethylene oxide and 1-3 mol of propylene oxide, preference being given to 2-propylheptanol alkoxylated with 1-15 mol of ethylene oxide and 1-3 mol of propylene oxide.

In the process according to the invention, polyalkylene oxide (A), graft monomer (B1) and, if appropriate, (B2), initiator (C) and, if appropriate, solvent (D) are heated to the selected mean polymerization temperature in a reactor.

According to the invention, the polymerization is carried out in such a way that an excess of polymer (polyalkylene oxide (A) and formed graft polymer) is constantly present in the reactor. The quantitative ratio of polymer to ungrafted monomer and initiator is generally ≥10:1, preferably ≥15:1 and more preferably ≥20:1.

The polymerization process according to the invention can in principle be carried out in various reactor types.

The reactor used is preferably a stirred tank in which the polyalkylene oxide (A), if appropriate together with portions, of generally up to 15 wt % of the particular total amount, of graft monomers (B), initiator (C) and solvent (D), are initially charged fully or partly and heated to the polymerization temperature, and the remaining amounts of (B), (C) and, if appropriate, (D) are metered in, preferably separately. The remaining amounts of (B), (C) and, if appropriate, (D) are metered in preferably over a period of ≥2 h, more preferably of ≥4 h and most preferably of ≥5 h.

In the case of the particularly preferred, substantially solvent-free process variant, the entire amount of polyalkylene oxide (A) is initially charged as a melt and the graft monomers (B1) and, if appropriate, (B2), and also the initiator (C) present preferably in the form of a from 10 to 50 wt % solution in one of the solvents (D), are metered in, the temperature being controlled such that the selected polymerization temperature, on average during the polymerization, is maintained with a range of especially +/−10° C., in particular +/−5° C.

In a further particularly preferred, low-solvent process variant, the procedure is as described above, except that solvent (D) is metered in during the polymerization in order to limit the viscosity of the reaction mixture. It is also possible to commence with the metered addition of the solvent only at a later time with advanced polymerization, or to add it in portions.

The polymerization can be effected under standard pressure or at reduced or elevated pressure. When the boiling point of the monomers (B) or of any diluent (D) used is exceeded at the selected pressure, the polymerization is carried out with reflux cooling.

It is preferred to add the dispersing component (comprising the dispersing agent optionally together with the co-dispersing agent) to the solid particles after the particles have been coated with the non-amphoteric, quaternizable and water-soluble polymer. However, alternatively, the dispersing component of the present invention can be added in the desired concentration to the polymer solution before the solid particles are added to the polymer solution in order to coat the particles with the polymer. Alternatively, the dispersing component comprising the dispersing agent with the optional co-dispersing agent, the coating polymer and the solid particles are all combined and mixed in a one-pot reaction to form the coated particles in the presence of the dispersing component comprising the dispersing agent and the optional co-dispersing agent.

Alternatively or additionally, the amount of coated particles in the inventive compositions comprising the coated particles and the dispersing component preferably is in the range of 1.0 to 50.0 wt %, preferably 5.0 to 40.0 wt %, more preferably 10.0 to 30.0 wt %, and even more preferably 20.0 to 27.0 wt % based on the total weight of the composition.

The amount of dispersing component, comprising, preferably consisting of, the combined amount of the at least one dispersing agent with the at least one optional co-dispersing agent, is in the range of 0.5 to 20.0 wt %, preferably 1.0 to 15.0 wt %, and even more preferably 2.0 to 10.0 wt %, or even 2.5 to 10.0 wt % based on the amount of particles, preferably pesticide, used in the aqueous compositions of the present invention. The non-amphoteric, quaternizable and water-soluble at 20° C. polymers are capable of inverting the charge of particles coated with said polymers. This is monitored by the zeta potential as measured on aqueous dispersions of the coated particles.

The measurement of the zeta potential represents a common method for the characterization of solid/liquid dispersions. For instance, dispersed particles can be electrostatically charged by absorption of ions on their surface. At the surface of these electrostatically charged particles, an electric double layer is formed which is solidly attached to the particles and causes an apparent increase in volume. This solid layer is covered by a mobile and diffuse layer of ions. The potential $\psi_0$ at the particle surface decreases within the solid layer of ions of the thickness δ linearly to the value $\psi_\delta$, while approximately falling exponentially to the value 0 in the diffuse layer. The difference in potential between the inner solid layer of ions $\psi_\delta$ and the position within the diffuse layer of ions, at which the potential has fallen to 1/e·$\psi_\delta$, is defined as the zeta potential.

The zeta potential can also be directly determined from the direction and velocity of migration of the dispersed particles in the electrical field, wherein the following equation applies:

$$\zeta = \frac{f \cdot \pi \cdot v \cdot \eta}{E \cdot \varepsilon}$$

ζ=zeta potential (in mV)
ε=dielectric constant of the dispersing agent
v=electrophoretic velocity of migration (in cm/s)
η=viscosity of dispersing agent (Poise, 1 Poise=0.1 Pa·s)
E=field strength (in mV)
f=numeric factor (friction number; "Reibungsfaktor"); depends on the shape, the conductivity and the size of the particles relative to the thickness of the diffuse double layer The measurement of the velocity of migration is carried out depending on the size of the corresponding particles either by light microscopy analysis or, particularly for smaller particles, by laser correlation spectroscopy.

The use of the polymers of the present invention cause an inversion of electric charge on the treated particles, for instance from a positive charge value to a negative one, or less preferred, from a negative charge value to a positive one. Preferred are changes from a negative to a positive zeta potential of the particles.

One preferred field of application of the compositions of the present invention comprising particles coated with at least one amphoteric, quaternizable and water soluble polymer and the dispersing component comprising the at least one dispersing agent is the preparation of pesticide compositions. In such pesticide compositions, the particles comprise or even consist of organic material which is a pesticide as the active ingredient, like preferably a fungicide.

The term pesticides usually refers to at least one active substance selected from the group of the fungicides, insecticides, nematicides, herbicides, safeners, biopesticides and/or growth regulators. Preferred pesticides are fungicides, insecticides, herbicides and growth regulators. Especially preferred pesticides are fungicides and insecticides. Herbicides are generally less preferred. Mixtures of pesticides of two or more of the abovementioned classes may also be used. The skilled worker is familiar with such pesticides, which can be found, for example, in the Pesticide Manual, 17th Ed. (2015), The British Crop Protection Council, London.

Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamid, clofentezin, hexythiazox, etoxazole, diafenthiuron, propargite, tetradifon, chlorofenapyr, DNOC, buprofezine, cyromazine, amitraz, hydramethylnon, acequinocyl, fluacrypyrim, rotenone, or their derivatives.

Suitable fungicides are fungicides from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles.

Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones)phenyl]-1-cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl)

phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)propan-2-ol, 2-[2-chloro-4-(4-chlorophenoxy) phenyl]-3-methyl-1-(1,2,4-triazol-1-yl)butan-2-ol, 2-[4-(4-chlorophenoxy)-2-(trifluoromethyl)phenyl]-1-(1,2,4-triazol-1-yl)pentan-2-ol, 2-[4-(4-fluorophenoxy)-2-(trifluoromethyl)phenyl]-1-(1,2,4-triazol-1-yl)propan-2-ol, 2-[2-chloro-4-(4-chlorophenoxy)phenyl]-1-(1,2,4-triazol-1-yl)pent-3-yn-2-ol); imidazoles: imazalil, pefurazoate, prochloraz, triflumizol; pyrimidines, pyridines and piperazines: fenarimol, nuarimol, pyrifenox, triforine, [3-(4-chloro-2-fluoro-phenyl)-5-(2,4-difluorophenyl)isoxazol-4-yl]-(3-pyridyl)methanol;

The above pesticides and their combinations thereof represent preferred organic material that can be used as particles treated, preferably coated, with the non-amphoteric, quaternizable and water-soluble at 20° C. polymers of the present invention. Alternatively or additionally, seed can be treated.

The coated particles can be stored and used as powder or granules, preferably the coated particles can be stored and applied as aqueous suspensions (dispersions), preferably suspension concentrates (SC).

Preferred formulation examples generally include all possible types of suspensions (SC, OD, FS), but also wettable powders or dusts (WP, SP, SS, WS, DP, DS) or granules (GR, FG, GG, MG), which can be water-soluble or wettable. Usually the composition types (e.g. SC, OD, FS, WG, SG, WP, SP, SS, WS, GF) are employed diluted. Composition types such as DP, DS, GR, FG, GG and MG are usually used undiluted.

Due to the additional coating, the particles can be stored and used as formulations, preferably dispersions/suspensions, at higher concentrations and higher stability for extended periods of time as well as at lower particle size based on the inversion of surface charge. The consequence is a more homogeneous distribution of the particles with active ingredient and the reduced tendency of the particles to agglomerate.

On the other hand, despite such improvements, the coated particles still require further stabilization because otherwise slow agglomeration and sedimentation of the particles in aqueous formulation remains one limitation of the coated particles.

The stability of the aqueous dispersions is one key property of pesticide compositions because the active ingredients in the field of pest control are often only very poorly soluble in water or not even soluble at all. Nonetheless, suitable formulations of pesticide compositions allowing straight-forward storage and application in the strict absence of organic solvents are an important requirement for state-of-the-art agrochemical pesticide formulations.

The present inventors have now further demonstrated in their studies that the additional presence of selected dispersing components comprising special dispersing agents in the compositions of the present invention, optionally with further co-dispersing agents, indeed allows further improving the stability of the coated particles in the compositions. Particularly, the storage stability of the compositions, for instance when formulated as suspension concentrates can be significantly improved by the presence of at least one suitable dispersing component as it has been monitored by measuring the sedimentation behavior of the coated particles over extended periods of time.

In this regard, the present inventors have found that the usual dispersing components are not applicable and incapable of further stabilizing the coated particles displaying inverted zeta potential. Rather, only very few types of dispersing components and selected individual compounds thereof are in fact suitable for further improving the stability of the particles when coated with non-amphoteric, quaternizable and water-soluble polymers.

For instance, it has been found that the commonly applied (co-)dispersing agents in pesticide formulations, like naphthalenesulphonic acid condensation type-stabilizers (e.g. Tamol DN®; BASF SE), when used without the dispersing agents according to the present invention, will be able to only insufficiently stabilize coated particles to a limited extent. In contrast thereto, the present inventors have found that the special dispersing components of the present invention, when the dispersing agents in the dispersing component are used either alone or in combination with the common co-dispersing agents, will provide much better stabilization of the coated particles.

Optionally, the aqueous compositions of the present invention comprise additional auxiliaries.

Examples for suitable auxiliaries are solvents, solid carriers, or emulsifiers (such as further solubilizers, protective colloids, surfactants and adhesion agents) in addition to the dispersing agents according to the present invention, organic and anorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols (such as ethylene glycol or 1,2-propylene glycol), ketones such as cyclohexanone and gamma-butyrolactone, fatty acid dimethylamides, fatty acids and fatty acid esters and strongly polar solvents, e.g. amines such as N-methylpyrrolidone. Preferred solvent is water.

Examples for suitable thickeners (i.e. compounds that impart a modified flowability to the compositions, i.e. high viscosity under static conditions and low viscosity during agitation) are polysaccharides and organic and anorganic clays such as Xanthan gum (Kelzan®, CP Kelco, U.S.A.), Rhodopol®23 (Rhodia, France), Veegum® (R.T. Vanderbilt, U.S.A.) or Attaclay® (Engelhard Corp., NJ, USA).

Bactericides may be added for preservation and stabilization of the compositions. Examples for suitable bactericides are those based on dichlorophene and benzylalcohol hemi formal (Proxel® from ICI or Acticide®RS from Thor Chemie and Kathon®MK from Rohm & Haas) and isothiazolinone derivatives such as alkylisothiazolinones and benzisothiazolinones (Acticide®MBS from Thor Chemie).

Examples for suitable anti-freezing agents are ethylene glycol, propylene glycol, urea and glycerin.

Examples for anti-foaming agents are silicone emulsions (such as e.g. Silikon® SRE, Wacker, Germany or Rhodorsil®, Rhodia, France; e.g. Agnique® DFM 111S and Agnique® ST2434 from BASF Corp. USA), long chain alcohols, fatty acids, salts of fatty acids, fluoroorganic compounds and mixtures thereof.

Examples of colorants are both sparingly water-soluble pigments and water-soluble dyes. Examples which may be mentioned are the dyes known under the names Rhodamin B, C.I. Pigment Red 1 12 and C.I. Solvent Red 1, and also pigment blue 15:4, pigment blue 15:3, pigment blue 15:2, pigment blue 15:1, pigment blue 80, pigment yellow 1, pigment yellow 13, pigment red 1 12, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Important features of the coated particles of the present invention when further stabilized by the selected dispersing components of the present invention are even more homogeneous formulation and application of the particles, particularly when spraying, which also has the additional effect that even better adhesion of the coated particles on the treated plants, the treated seed and/or the agricultural area results in more sustained treatment of the plants and the fields with the corresponding pesticide. Accordingly, improved rain fastness is one important advantage of the compositions of the present invention achieved by adding selected dispering components.

The application of the coated pesticides can optionally be achieved by spraying aqueous dispersions over the plants and the agricultural areas like fields, gardens, vinyards, acres, forests, greens and the like.

Needless to say that more homogeneous distribution of pesticides and improved rain fastness lead to more effective and more sustained pesticidal treatment while the overall amount of pesticide to be applied can be potentially reduced without loss of pesticidal efficacy.

Another preferred field of application of the compositions comprising particles coated with at least one nonamphoteric, quaternizable and water-soluble polymer and at least one selected dispersing component relates to the use of particles which comprise or even consist of a pharmaceutically active compound or a cosmetic material.

Examples

1. General method for the coating of pesticide particles with non-amphoteric, quaternizable and water-soluble at 20° C. polymer comprising an additional dispersing component.

For the preparation of an aqueous suspension concentrate (SC) comprising coated particles comprising an additional dispersing component, the following components are mixed for 120 min in a dispersing device (LAU disperser, model DAS H [/A] 200-K).

| | |
|---|---|
| Active ingredient (AI) | 25 wt % |
| Dispersing component | 2.5 wt % |
| Polymer | 0.25-2.5 wt % |
| Defoamer | 0.3 wt % |
| Water (pH = 9) | ad 100% |

The defoamer used: Agnique® DFM 111S (silicon emulsion, BASF SE).

The suspension concentrate (80 g) prepared according to the composition above is milled with 80 g glass beads (d=3 mm) in a 100 ml Teflon bottle in the LAU disperser for 90 to 150 min (cooling level 2). The glass beads are subsequently separated by sieving.

2. Method for the measurement of zeta potential of coated/uncoated particles

The determination of the zeta potential of the aqueous suspensions comprising active ingredient has been carried out with a Coulter DELSA 440 SX according to the manufacturer's instructions. Untreated particles have a negative surface charge whereas the particles coated with a non-amphoteric, quaternizable, water-soluble polymer will have a positive surface charge.

3. Characterization of the stability of coated particles in the presence of various dispersing components The particle size distributions (PSD) of the samples have been analyzed using a Malvern Mastersizer 3000.

TABLE 1

Aqueous compositions of coated particles comprising various dispersing components

| | Active ingredient [wt %] | | Coating polymer [wt %] | | | Dispersing component [wt %] |
|---|---|---|---|---|---|---|
| Inventive Example | | | | | | |
| IE1 | Azoxystrobin | 25 | Lupasol ® WF | 2.5 | 1 | 2.5 |
| IE2 | Azoxystrobin | 25 | Lupasol ® WF | 2.5 | 2 | 2.5 |
| IE3 | Chlorothalonil | 25 | Lupasol ® WF | 2.5 | 1 | 2.5 |
| IE4 | Chlorothalonil | 50 | Lupasol ® WF | 3.75 | 2 | 5.0 |
| IE5 | Azoxystrobin | 50 | Lupasol ® WF | 3.75 | 2 | 5.0 |
| IE6 | Deltamethrin | 25 | Lupasol ® WF | 2.5 | 1 | 2.5 |
| IE7 | Epoxyconazole | 25 | Lupasol ® WF | 2.5 | 1 | 5.0 |
| IE8 | Boscalid | 25 | Lupasol ® WF | 1.75 | 1 | 2.5 |
| IE9 | Azoxystrobin | 25 | Lupasol ® WF | 2.5 | 4 | 2.5 |
| IE10 | Azoxystrobin | 25 | Lupasol ® WF | 2.5 | 5 | 2.5 |
| IE11 | Azoxystrobin | 25 | Lupasol ® WF | 2.5 | 6 | 2.5 |
| IE12 | Azoxystrobin | 25 | Lupasol ® WF | 2.5 | 7 | 2.5 |
| IE13 | Azoxystrobin | 25 | Lupasol ® WF | 2.5 | 8 | 2.5 |
| IE14 | Azoxystrobin | 25 | Lupasol ® PS | 2.5 | 2 | 2.5 |
| IE15 | Azoxystrobin | 25 | Lupasol ® SK | 2.5 | 2 | 2.5 |
| IE16 | Azoxystrobin | 25 | Lupasol ® FG | 2.5 | 2 | 2.5 |
| IE17 | Azoxystrobin | 25 | Lupasol ® G100 | 2.5 | 2 | 2.5 |
| IE18 | Azoxystrobin | 25 | Lupasol ® WF | 2.5 | 9 | 2.5 |
| IE19 | Azoxystrobin | 25 | Lupasol ® WF | 2.5 | 10 | 2.5 |
| IE20 | Azoxystrobin | 25 | Lupasol ® WF | 2.5 | 11 | 2.5 |
| IE21 | Azoxystrobin | 25 | Lupasol ® WF | 2.5 | 3 | 2.5 |
| Non-Inventive Example | | | | | | |
| NIE1 | Azoxystrobin | 25 | Lupasol ® WF | 1.75 | 12 | 2.5 |
| NIE2 | Azoxystrobin | 25 | Lupasol ® WF | 2.5 | 12 | 5.0 |
| NIE3 | Boscalid | 25 | Lupasol ® WF | 1.75 | 12 | 2.5 |
| NIE4 | Chlorothalonil | 25 | Lupasol ® WF | 2.5 | 12 | 5.0 |
| NIE5 | Azoxystrobin | 25 | Lupasol ® WF | 2.5 | 13 | 2.5 |
| NIE6 | Azoxystrobin | 25 | Lupasol ® WF | 2.5 | 14 | 2.5 |
| NIE7 | Azoxystrobin | 25 | Lupasol ® WF | 2.5 | 15 | 2.5 |
| NIE8 | Chlorothalonil | 25 | Lupasol ® WF | 2.5 | 15 | 2.5 |
| NIE9 | Azoxystrobin | 25 | Lupasol ® PS | 2.5 | 15 | 2.5 |
| NIE10 | Azoxystrobin | 25 | Lupasol ® SK | 2.5 | 15 | 2.5 |
| NIE11 | Azoxystrobin | 25 | Lupasol ® WF | 2.5 | 16 | 2.5 |
| NIE12 | Azoxystrobin | 25 | Lupasol ® WF | 1.75 | 17 | 5.0 |
| NIE13 | Azoxystrobin | 25 | — | — | 18 | 2.5 |
| NIE14 | Pyraclostrobin | 25 | — | — | 18 | 5.0 |
| NIE15 | Deltamethrin | 25 | — | — | 18 | 2.5 |
| NIE16 | Fluxapyroxad | 25 | — | — | 18 | 2.5 |

Azoxystrobin was supplied from Cheminova A/S;

Boscalid was supplied from BASF SE;

Chlorothalonil was supplied from Syngenta AG;

Deltamethrin was supplied from Interchim;

Epoxiconazole was supplied from Jiangsu Greenscie Chemical Co. Ltd.;

Pyraclostrobin was supplied from BASF SE

Fluxapyroxad was supplied from BASF SE

TABLE 2

Properties of polyethyleneimine coating polymers

| Polymer coating | concentration [%]° | water content [%]°° | M [g/mol] | Viscosity* [mPas] | pH** |
|---|---|---|---|---|---|
| Lupasol ® FG | 99 | 1 | 800 | approx. 1500 | 11 |
| Lupasol ® G100 | 50 | 50 | 5000 | approx. 1100 | 11 |
| Lupasol ® WF | 99 | 1 | 25000 | >200000 | 11 |
| Lupasol ® PS | 33 | 67 | 750000 | approx. 1700 | 11 |
| Lupasol ® SK | 24 | 76 | 2000000 | approx. 700 | 7 |

°measured according to ISO 3251
°°measured according to DIN 53715, K. Fischer
*measured according to ISO 2555, Brookfield
**measured according to DIN 19268, 1% dry substance in distilled water Composition of Dispersing Components:

Dispersing component 1: Pluriol® E 6000 (40 wt %) (PEG 6000, BASF SE)/Vinyl Acetate (60 wt %);

Dispersing component 2: Pluriol® E 6000 (40 wt %) (PEG 6000, BASF SE)/Vinyl Acetate (60 wt %); 14 wt % Lutensol® XL 100 (alcohol alkoxylate, BASF SE);

Dispersing component 3: Pluriol® E 4000 (40 wt %) (PEG 4000, BASF SE)/Vinyl Acetate (60 wt %);

Dispersing component 4: Pluriol® E 6000 (40 wt %) (PEG 6000, BASF SE)/Vinyl Acetate (60 wt %); 14 wt % Lutensol® XP 60 (alcohol ethoxylate, BASF SE);

Dispersing component 5: Pluriol® E 6000 (40 wt %) (PEG 6000, BASF SE)/Vinyl Acetate (60 wt %); 14 wt % Emulan® P (alcohol ethoxylate, BASF SE);

Dispersing component 6: Pluriol® E 6000 (40 wt %) (PEG 6000, BASF SE)/Vinyl Acetate (60 wt %); 14 wt % Plurafac® LF 221 (alcohol alkoxylate, BASF SE);

Dispersing component 7: Pluriol® E 6000 (40 wt %) (PEG 6000, BASF SE)/Vinyl Acetate (60 wt %); 14 wt % Plurafac® LF 300 (alcohol alkoxylate, BASF SE);

Dispersing component 8: Pluriol® E 6000 (40 wt %) (PEG 6000, BASF SE)/Vinyl Acetate (60 wt %); Pluronic® PE 10500 (block copolymer, BASF SE) (1:1);

Dispersing component 9: Pluriol® E 6000 (40 wt %) (PEG 6000, BASF SE)/Vinyl Acetate (60 wt %); 14 wt % Lutensol® TO 8 (alcohol ethoxylate, BASF SE);

Dispersing component 10: Pluriol® E 6000 (40 wt %) (PEG 6000, BASF SE)/Vinyl Acetate (60 wt %); 14 wt % Lutensol® XL 70 (alcohol alkoxylate, BASF SE);

Dispersing component 11: Pluriol® E 6000 (40 wt %) (PEG 6000, BASF SE)/Vinyl Acetate (60 wt %); 14 wt % Plurafac® LF 120 (alcohol alkoxylate, BASF SE);

Dispersing component 12: Tamol® DN (Phenol sulphonic acid condensation product, sodium salt, BASF SE);

Dispersing component 13: Pluronic® PE 6400 (Propylene oxide ethylene oxide block polymer, about 2900 g/mol, BASF SE);

Dispersing component 14: Pluronic® PE 10300 (Propylene oxide ethylene oxide block polymer, about 4950 g/mol, BASF SE);

Dispersing component 15: Pluronic® PE 10500 (Propylene oxide ethylene oxide block polymer, about 6500 g/mol, BASF SE);

Dispersing component 16: Tamol® NN 8906 (Naphthalene sulphonic acid condensation product, sodium salt, BASF SE);

Dispersing component 17: Pluronic® PE 10500 (Propylene oxide ethylene oxide block polymer, about 6500 g/mol, BASF SE)/Tamol® NN 8906 (1:1) (Naphthalene sulphonic acid condensation product, sodium salt, BASF SE);

Dispersing component 18: Pluriol® E 6000 (40 wt %) (PEG 6000, BASF SE)/Vinyl Acetate (60 wt %); 14 wt % Lutensol® XL 100 (alcohol alkoxylate, BASF SE);

TABLE 3

Viscosity and sedimentation behavior of coated particles comprising various dispersing components

| | Viscosity after milling | Sedimentation behavior (for 24 h after preparation and before storage) | | | Sedimentation behavior (after storage for 14 days at −10° C. to 40° C.) | | | Sedimentation behavior (after storage for 14 days at 54° C.) | | |
|---|---|---|---|---|---|---|---|---|---|---|
| | | | PSD [d$_{90}$; μm] | PSD [d$_{50}$; μm] | | PSD [d$_{90}$; μm] | PSD [d$_{50}$; μm] | | PSD [d$_{90}$; μm] | PSD [d$_{50}$; μm] |
| IE1 | 1 | 2 | 4.2 | 1.5 | 1 | 3.7 | 1.7 | 3 | 3.6 | 1.4 |
| IE2 | 1 | 2 | 5.4 | 1.9 | 1 | 4.3 | 1.9 | 3 | 3.8 | 1.7 |
| IE3 | 2 | 2 | 6.8 | 2.4 | 1 | 6.6 | 2.3 | 3 | 6.6 | 2.3 |
| IE4 | 3 | 2 | 7.2 | 2.8 | 3 | 7.2 | 2.9 | 3 | 7.4 | 3.0 |
| IE5 | 3 | 2 | 7.6 | 2.8 | 1 | 6.8 | 2.5 | 3 | 7.9 | 3.1 |
| IE6 | 1 | 2 | 8.9 | 2.7 | 1 | 7.6 | 2.6 | 3 | 5.7 | 2.1 |
| IE7 | 1 | 1 | 5.8 | 2.0 | 2 | 6.0 | 2.2 | 3 | 5.9 | 2.1 |
| IE8 | 1 | 1 | 6.9 | 2.8 | 2 | 7.5 | 3.1 | 3 | 7.1 | 2.9 |
| IE9 | 1 | 2 | 5.4 | 1.6 | 1 | 3.5 | 1.6 | 3 | 3.1 | 1.3 |
| IE10 | 1 | 2 | 5.1 | 1.6 | 1 | 3.7 | 1.6 | 3 | 3.7 | 1.3 |
| IE11 | 1 | 2 | 5.7 | 1.6 | 1 | 4.1 | 1.7 | 3 | 3.0 | 1.3 |
| IE12 | 1 | 2 | 5.3 | 1.6 | 1 | 3.7 | 1.6 | 3 | 3.2 | 1.3 |
| IE13 | 1 | 1 | 5.2 | 1.6 | 1 | 4.1 | 1.6 | 2 | 3.2 | 1.3 |
| IE14 | 1 | 1 | 5.7 | 2.1 | 1 | 4.6 | 2.0 | 3 | 3.9 | 1.9 |
| IE15 | 1 | 1 | 5.5 | 1.9 | 1 | 4.5 | 1.9 | 3 | 3.8 | 1.8 |

TABLE 3-continued

Viscosity and sedimentation behavior of coated particles comprising various dispersing components

|  | Viscosity after milling | Sedimentation behavior (for 24 h after preparation and before storage) | | | Sedimentation behavior (after storage for 14 days at −10° C. to 40° C.) | | | Sedimentation behavior (after storage for 14 days at 54° C.) | | |
|---|---|---|---|---|---|---|---|---|---|---|
|  |  |  | PSD [$d_{90}$; μm] | PSD [$d_{50}$; μm] |  | PSD [$d_{90}$; μm] | PSD [$d_{50}$; μm] |  | PSD [$d_{90}$; μm] | PSD [$d_{50}$; μm] |
| IE16 | 1 | 1 | 6.1 | 2.4 | 1 | 5.3 | 2.5 | 3 | 4.3 | 2.3 |
| IE17 | 1 | 1 | 6.0 | 2.2 | 1 | 5.1 | 2.2 | 3 | 4.0 | 2.0 |
| IE18 | 1 | 2 | 6.4 | 2.1 | 1 | 4.4 | 1.9 | 3 | 4.1 | 1.7 |
| IE19 | 1 | 2 | 5.3 | 1.6 | 1 | 3.5 | 1.6 | 3 | 3.1 | 1.3 |
| IE20 | 1 | 2 | 5.4 | 1.6 | 1 | 3.6 | 1.6 | 3 | 2.9 | 1.3 |
| IE21 | 1 | 2 | 8.2 | 2.8 | 3 | 7.6 | 2.7 | 3 | 6.5 | 2.1 |
| NIE1 | 2 | n.d. | 15.2 | 8.8 | x | x | x | x | x | x |
| NIE2 | 3 | x | x | x | x | x | x | x | x | x |
| NIE3 | 3 | x | x | x | x | x | x | x | x | x |
| NIE4 | 3 | x | x | x | x | x | x | x | x | x |
| NIE5 | 3 | x | x | x | x | x | x | x | x | x |
| NIE6 | 1 | 1 | 4.6 | 1.9 | 1 | 154 | 42.7 | 2 | 5.8 | 2.8 |
| NIE7 | 1 | 1 | 4.1 | 1.6 | 2 | 67.5 | 3.1 | 2 | 77.5 | 2.0 |
| NIE8 | 1 | 2 | 7.1 | 2.6 | 2 | 12.6 | 2.7 | 4 | x | x |
| NIE9 | 1 | 1 | 4.9 | 1.8 | 2 | 87.5 | 3.2 | 2 | 39.4 | 2.4 |
| NIE10 | 1 | 1 | 5.1 | 1.7 | 2 | 25.6 | 2.9 | 2 | 12.6 | 1.9 |
| NIE11 | 2 | 2 | 8.4 | 2.6 | 1 | 25.8 | 3.4 | 2 | 10.8 | 2.5 |
| NIE12 | 1 | 1 | 5.0 | 1.9 | 1 | 16.5 | 2.7 | 4 | x | x |
| NIE13 | 1 | 2 | 4.6 | 1.5 | 1 | 3.3 | 1.6 | 4 | x | x |
| NIE14 | 1 | 2 | 6.1 | 2.4 | 3 | 6.5 | 2.7 | 4 | x | x |
| NIE15 | 1 | 2 | 8.4 | 2.3 | 1 | 53.0 | 2.9 | 3 | 4.7 | 1.7 |
| NIE16 | 1 | 3 | 8.1 | 2.9 | 3 | 7.3 | 2.7 | 4 | x | x |

Analysis of Viscosity:
Technical meaning of values ranging on scale from 1 to 3; 1=very soft; 2=soft; 3=pasty/solid;

Analysis of Sedimentation Behavior:
Values ranging on a scale from 1 to 3; 1=excellent; 2=good; 3=poor; a value of 1—excellent—is attributed to a sample in which the particles can be shaken up immediately; a value of 2—good—is attributed to a sample in which the particles can be shaken up quickly by less than 50 rounds of heavy shaking; a value of 3—poor—is attributed to a sample in which the particles could only be shaken up by at least 50 rounds or more of heavy shaking; samples for which shaking up the particles has been impossible even after extended periods of heavy shaking have not been included in this analysis;

TABLE 4

Determination of zeta potential for aqueous compositions of coated particles comprising various dispersing components

| | Sample | | | | | | | | |
|---|---|---|---|---|---|---|---|---|---|
| | IE1 | IE3 | IE6 | IE7 | IE8 | IE22 | IE23 | IE24 | IE25 |
| Zeta potential [mV] | +43 | +45 | +55 | +43 | +14 | +34 | +43 | +44 | +43 |

The invention claimed is:

1. An aqueous composition comprising:
from 20 to 27 wt %, based on the total weight of the composition, of particles coated with at least one non-amphoteric, quaternizable polymer which is water soluble at 20° C., wherein the at least one non-amphoteric, quaternizable polymer is present in an amount of from 0.25 to less than 4 wt %, based on the total weight of the composition, and
from 2 to 5 wt %, based on the total weight of the composition, of at least one dispersing component wherein the dispersing component comprises a dispersing agent selected from an amphiphilic graft polymer based on water soluble polyalkylene oxides (A) as a graft base and side chains formed by polymerization of a vinyl ester component (B), said polymer having an average of ≤1 graft site per 50 alkylene oxide units and a mean molar mass $M_w$ of from 3000 to 100 000;
wherein the particles are selected from the group consisting of Deltamethrin, Boscalid, Fluxapyroxad, Chlorothalonil, Epoxiconazole, Mefentrifluconazole, Strobilurins, Azoxystrobin, Dimoxystrobin, and combinations thereof; and
wherein the coated particles have a positive zeta potential in the presence of the at least one dispersing component.

2. The aqueous composition according to claim 1, wherein the amphiphilic graft polymer has a polydispersity $M_w/M_n$ of <3.

3. The aqueous composition according to claim 1, wherein the amphiphilic graft polymer comprises <10 wt % of polyvinyl ester (B) in ungrafted form.

4. The aqueous composition according to claim 1, wherein the amphiphilic graft polymer has:
(A) from 20 to 70 wt % of the water-soluble polyalkylene oxide as the graft base; and
(B) side chains formed by free-radical polymerization of from 30 to 80 wt % of the vinyl ester component, composed of:
(B1) from 70 to 100% wt % of vinyl acetate and/or vinyl propionate; and
(B2) from 0 to 30 wt % of a further ethylenically unsaturated monomer in the presence of (A).

5. The aqueous composition according to claim 1, wherein the amphiphilic graft polymer comprises from 25 to 60 wt % of the graft base (A) and from 40 to 75 wt % of the vinyl ester component (B).

6. The aqueous composition according to claim 4, wherein the vinyl ester component (B) of the amphiphilic graft polymer comprises from 70 to 100 wt % of vinyl acetate (B1) and from 0 to 30 wt % of a C1 to C8 alkyl acrylate (B2).

7. The aqueous composition according to claim 1, wherein the dispersing agent is selected from an amphiphilic graft polymer obtained from a reaction of polyethylene oxide 6000 and vinyl acetate with a weight ratio of PEG 6000 to vinyl acetate of 40 to 60, and the dispersing component optionally comprises further co-dispersing agents.

8. The aqueous composition according to claim 1, wherein the non-amphoteric, quaternizable polymer being water soluble at 20° C. is selected from the group consisting of polyvinylamines, polyvinylamidoamines, polyethyleneimines, polypropyleneimines, polyamidoamines or polyureaamines, cationic copolymers comprising polymerisable monomers selected from the group consisting of vinylpyrrolidone, methacrylamide, vinyl imidazole, quaternized vinyl imidazole and combinations thereof, cationic copolymers comprising the cationic copolymers comprising polymerizable monomers selected from the group consisting of vinylpyrrolidone and quaternized vinyl imidazole, cationic copolymers comprising polymerizable monomers selected from the group consisting of vinylpyrrolidone and quaternized dimethylaminoethyl methacrylate (DMAEMA), cationic copolymers comprising polymerizable monomers selected from the group consisting of vinyl caprolactam, vinylpyrrolidone and quaternized vinyl imidazole, and combinations of said polymers.

9. The aqueous composition according to claim 1, wherein the particles have a median particle size ($D_{50}$) in a range of 0.1 to 50 μm and/or a median particle size ($D_{90}$) in a range of 0.1 to 50 μm as measured with a Malvern Mastersizer 3000.

10. The aqueous composition according to claim 1, wherein the particles have a median particle size ($D_{50}$) in a range of 0.5 to 20 μm and/or a median particle size ($D_{90}$) in a range of 0.5 to 20 μm as measured with a Malvern Mastersizer 3000.

11. The aqueous composition according to claim 1, wherein the particles have a median particle size ($D_{50}$) in a range of 1.0 to 10 μm and/or a median particle size ($D_{90}$) in a range of 1.0 to 15 μm as measured with a Malvern Mastersizer 3000.

12. The aqueous composition according to claim 1, wherein the particles have a median particle size ($D_{50}$) in a range of 1.5 to 5 μm and/or a median particle size ($D_{90}$) in a range of 1.5 to 10 μm as measured with a Malvern Mastersizer 3000.

13. A method of using the aqueous composition according to claim 1, the method comprising using the aqueous composition for a preparation of an agrochemical, cosmetic or pharmaceutical formulation.

14. A method of using at least one dispersing component according to claim 1, the method comprising using the at least one dispersing component for dispersing a non-amphoteric, quaternizable polymer which is water soluble at 20° C. in an aqueous composition.

* * * * *